(12) United States Patent
Boyd

(10) Patent No.: US 12,427,273 B1
(45) Date of Patent: Sep. 30, 2025

(54) METHODS FOR TREATING RESPIRATORY DISTRESS AND COMPOSITIONS FOR USE IN THE SAME

(71) Applicant: John E. Boyd, Old Greenwich, CT (US)

(72) Inventor: John E. Boyd, Old Greenwich, CT (US)

( * ) Notice: Subject to any disclaimer, the term of this patent is extended or adjusted under 35 U.S.C. 154(b) by 1181 days.

(21) Appl. No.: 17/302,643

(22) Filed: May 8, 2021

Related U.S. Application Data

(60) Provisional application No. 62/704,563, filed on May 15, 2020.

(51) Int. Cl.
*A61M 16/00* (2006.01)
*A61M 16/06* (2006.01)

(52) U.S. Cl.
CPC .... *A61M 16/0006* (2014.02); *A61M 16/0054* (2013.01); *A61M 16/06* (2013.01); *A61M 2202/0488* (2013.01)

(58) Field of Classification Search
CPC .............. A61M 16/00; A61M 16/0006; A61M 16/021; A61M 16/022; A61M 16/0054; A61M 16/06; A61M 2202/0488; A61H 9/00; A61H 9/0007; A61H 9/005; A61H 9/0078; A61H 9/0092
See application file for complete search history.

(56) References Cited

U.S. PATENT DOCUMENTS

| | | | |
|---|---|---|---|
| 6,676,614 B1 * | 1/2004 | Hansen | A61H 23/04 601/44 |
| 6,694,978 B1 | 2/2004 | Bennarsten | |
| 6,705,319 B1 | 3/2004 | Wodicka et al. | |
| 7,011,094 B2 | 3/2006 | Rapacki et al. | |
| 7,398,782 B2 | 7/2008 | Tanaka | |
| 7,588,033 B2 | 9/2009 | Wondka | |
| 7,909,031 B2 | 3/2011 | Shaffer et al. | |
| 7,931,607 B2 | 4/2011 | Biondo et al. | |
| 8,221,772 B2 | 7/2012 | Johnson et al. | |
| 8,347,883 B2 | 1/2013 | Bird | |
| 8,800,557 B2 | 8/2014 | Andreiux | |
| 8,876,791 B2 | 11/2014 | Wondka et al. | |
| 8,955,518 B2 | 2/2015 | Wondka | |
| 9,295,795 B2 | 3/2016 | Christopher et al. | |
| 9,352,112 B2 | 5/2016 | Sederstrom et al. | |
| 9,358,358 B2 | 6/2016 | Wondka et al. | |
| 9,913,953 B2 | 3/2018 | Moody et al. | |
| 10,406,200 B2 | 9/2019 | Arnold et al. | |
| 10,441,735 B1 | 10/2019 | Zhou | |
| 10,532,066 B2 | 1/2020 | Voelker et al. | |
| 2012/0053513 A1 * | 3/2012 | Tada | A61M 16/0404 604/514 |
| 2015/0196682 A1 * | 7/2015 | Tsai | A61K 38/38 514/15.2 |
| 2017/0020768 A1 * | 1/2017 | Palmer | A61H 31/02 |
| 2017/0239385 A1 | 8/2017 | Ingenito et al. | |
| 2019/0274951 A1 * | 9/2019 | Sznitman | A61K 35/42 |
| 2023/0226293 A1 * | 7/2023 | Ashkenazi | A61M 16/022 128/204.21 |

FOREIGN PATENT DOCUMENTS

| | | |
|---|---|---|
| WO | 2006071796 A2 | 7/2006 |
| WO | 2013188845 A1 | 12/2013 |

OTHER PUBLICATIONS

"Exogenous surfactant in acute respiratory distress syndrome: more is better", A. Anzueto European Respiratory Journal 2002 19: 787-789; DOI: 10.1183/09031936.02.00284902Av.
"A Clinical Trial of Nebulized Surfactant for the Treatment of Moderate to Severe COVID-19 (COVSurf)", NIH Clinical Trials, Identifier: NCT04362059, Apr. 24, 2020/May 28, 2020.
"Surfactant Worth Studying As Treatment for Covid-19-Related ARDS", Mass General Advances in Motion, May 8, 2020.
"Lung Surfactant for Pulmonary Barrier Restoration in Patients With COVID-19 Pneumonia", by Mirastschijski et al., Frontiers in Medicine, 2020: 7: 254 (PMCID: PMC7256165), May 22, 2020.
Windtree to Pursue Clinical Study of Lung Injury Treatment in COVID-19 Patients with its KL4 Surfactant Therapy, Windtree Press Release, Mar. 24, 2020.
"Performing Postural Drainage for People With COPD", verywellheath. com, Jul. 24, 2020.
"Technical specifications of medical devices for the case management of COVID-19 in healthcare settings". WHO (interim recommendations, Mar. 4, 2020).
"Ventilation with Lower Tidal Volumes as Compared with Traditional Tidal Volumes for Acute Lung Injury and the Acute Respiratory Distress Syndrome", The New England Journal of Medicine 2000; 342; 1301-1308.
"Oxygenation and Ventilation of Covid-19 Patients: Module 3: Ventilation Equipment", American Heart Association.
How 'Lung Washing' Helps You Breathe Again, Health Essentials from Cleveland Clinic, Aug. 6, 2014.
"Whole lung lavage—technical details, challenges and management of complications", Awab et al., Journal of Thoracic Disease, Jun. 2017; 9(6); 1697-1706.
"Mechanical Ventilation", Patient Education/Information Series, American Thoracic Society, 2017.
"Curosurf® in Adult Acute Respiratory Distress Syndrome Due to COVID-19 (Caards-1)", NIH Clinical Trials, Identifier: NCT04384731, May 12, 2020/Feb. 3, 2021.
"London's Exogenous Surfactant Study for COVID19 (LESSCOVID)", NIH Clinical Trials, Identifier: NCT04375735, May 5, 2020/Jun. 11, 2020.
"Could HFCWO Change The Face of Covid Mucus Removal?", by Phil Baur, ClarityGlobalGroup, Dec. 9, 2020.
"Lung Ultrasound to Guide Surfactant Therapy (ECOSURF)", NIH Clinical Trials, Identifier: NCT04330443, Apr. 1, 2020/May 15, 2020.

(Continued)

*Primary Examiner* — Colin W Stuart

(57) ABSTRACT

Methods for treating respiratory distress such as ARDS using foaming agent(s) (e.g., natural and/or synthetic surfactant(s)) and/or external energy (e.g., vibration, acoustic, etc.) and compositions and systems configured for performing the same.

20 Claims, No Drawings

(56) References Cited

OTHER PUBLICATIONS

"Poractant Alfa—Curosurf and SARS-COV-19 ARDS (Covid-19)", NIH Clinical Trials, Identifier: NCT04502433, Aug. 6, 2020/Jan. 20, 2021.

"Surfactant-BL in Adult Acute Respiratory Distress Syndrome Due to COVID-19", NIH Clinical Trials, Identifier: NCT04568018, Sep. 29, 2020/Sep. 29, 2020.

"The Safety and Preliminary Efficacy of Lucinactant in Adults With COVID-19", NIH Clinical Trials, Identifier: NCT04389671, May 15, 2020/Oct. 8, 2020.

* cited by examiner

METHODS FOR TREATING RESPIRATORY DISTRESS AND COMPOSITIONS FOR USE IN THE SAME

RELATED APPLICATIONS

This application claims the benefit of and priority to U.S. Provisional Application No. 62/704,563, entitled "Methods for Treating Respiratory Distress and Compositions for Use in the Same", filed May 15, 2020, the entire contents of each U.S. provisional application hereby incorporated by reference.

TECHNICAL FIELD

The invention generally relates to methods for treating respiratory distress and compositions and systems for use in the same.

BACKGROUND

Several publications are referenced in this application. The cited references describe the state of the art to which this invention pertains and are hereby incorporated by reference, particularly the systems, compositions and methods set forth in the detailed description and figures of each reference.

Pulmonary edema is the abnormal accumulation of fluid in the interstitium and air spaces of the lungs, which leads to impaired gas exchange and respiratory failure. Acute respiratory distress syndrome (ARDS) is a syndrome of acute respiratory failure caused by non-cardiogenic pulmonary edema. ARDS is a significant cause of acute respiratory failure that is often associated with multiple organ failure. Several clinical disorders can precipitate ARDS, including pneumonia, sepsis, aspiration of gastric contents, and major trauma. The most common cause of ARDS is bacterial or viral pneumonia. Physiologically, ARDS is characterized by increased permeability pulmonary edema, severe arterial hypoxemia, and impaired carbon dioxide excretion.

The lungs are large, paired, spongy, elastic organs. Lungs are positioned in the thoracic cavity and in contact with the walls of the thoracic cavity. Both the left and right lung is covered with a pleural membrane which forms a continuous sac that encloses the lung and also forms a lining for the thoracic cavity. Healthy lungs have an enormous surface area for gas exchange (e.g., the O2/CO2 exchange). Each lung comprises bronchi which branch into a multiplicity of smaller vessels referred to as bronchioles. Typically, there are more than one million bronchioles in each lung and each bronchiole ends in a cluster of extremely small air sacs referred to as alveoli.

Alveoli have an extremely thin, single layer of epithelial cells lining each alveolus wall and an extremely thin, single layer of epithelial cells lining the capillary walls that separate the air/gas in the alveolus from the circulating blood. Oxygen molecules in higher concentration can pass by simple diffusion through the two thin layers from the alveoli into the blood in the pulmonary capillaries, while carbon dioxide molecules in higher concentration can pass by simple diffusion through the two thin layers from the blood in the pulmonary capillaries into the alveoli.

An outbreak of a virulent respiratory virus, now known as Severe Acute Respiratory Syndrome (SARS), was identified in Hong Kong, China and a number of other countries around the world in 2003. Patients typically had symptoms including fever, dry cough, dyspnea, headache, and hypoxemia. Isolates of the SARS virus appear to have homology with at least the RNA polymerase gene of several known coronaviruses. In 2019, another outbreak of a virulent respiratory virus, now known as severe acute respiratory syndrome coronavirus-2 (SARS-COV-2 and often abbreviated as COVID-19), was identified and spread around the world in 2019/2020/2021. Patients typically had symptoms including fever, dry cough, and shortness of breath. As of Apr. 21, 2020, more than 2.53 million cases have been reported across 185 countries and territories, resulting in more than 174,000 deaths. As of Jul. 27, 2020, the numbers roses to more than 16 million cases have been reported across 188 countries and territories, resulting in more than 650,000 deaths. As of Apr. 12, 2021, the numbers rose to more than 136 million cases have been reported across 192 countries and territories, resulting in more than 2,944,366 deaths.

Virus infections including those caused by COVID-19 have caused certain individuals to have severe hypoxemia, even though their respiratory compliance (discussed below) may be normal. This results in the individual having to work hard to breath and the individual is often required to be admitted as a patient and intubated. Unfortunately, there have also been higher rates of mortality than expected among COVID-19 patients on ventilators, prompting some to question whether intubation protocols for ARDS patients are the right protocols. In fact, some have questioned whether high pressures forced into some patients' lung during certain ventilation protocols may actually be doing damage to the patients' lungs. Others have questioned the administration of pure or enhanced oxygen over time. See, "*Why does breathing pure oxygen kill you?*" BBC Science Forum. Jul. 17, 2020 and "*Oxygen Toxicity*" by Jeffery S. Copper and Neal Shah, NCBI Bookshelf ID: NBK430743; PMID: 28613494, Jul. 17, 2020.

There is a growing need for improved treatments for individuals having respiratory symptoms including those caused by pulmonary edema and particularly for treatment of individuals with ARDS caused by virus (e.g., COVID-19), bacterium and other pathogenic microorganisms and foreign substances and other ARDS and/or other respiratory failure symptoms/illnesses/diseases.

SUMMARY OF INVENTION

The invention relates to methods for treating individuals having respiratory distress and/or respiratory illness/symptom/disease and compositions and systems for use in the same.

One aspect of the invention relates to methods of treating an individual having at least one lower respiratory system region with at least one respiratory failure symptom, the method comprising administrating at least one foaming agent (e.g., natural and/or synthetic surfactants) to the at least one lower respiratory system region. Preferably, the method further comprises applying external energy (e.g., vibrational energy) to the at least one lower respiratory system region.

Another aspect of the invention relates to a method of treating an individual having at least one lower respiratory system region with at least one respiratory failure symptom/illness/disease, the method comprising:

(a) administrating at least one foaming agent (e.g., natural and/or synthetic surfactants) to the at least one lower respiratory system region; and (b) applying external energy to the at least one lower respiratory system region including to at least one alveolus in an effective amount and for an effective time period to reduce the at least one respiratory failure symptom/illness/disease.

Another aspect of the invention relates to a method of treating an individual having at least one lower respiratory system region with ARDS symptoms, the method comprising:
(a) administrating at least one foaming agent (e.g., natural and/or synthetic surfactants) to the at least one lower respiratory system region; and, preferably,
(b) applying external energy to the at least one lower respiratory system region including the at least one alveolus in an effective amount and for an effective time period to reduce the ARDS symptoms.

Yet another aspect of the invention relates to compositions comprising an aerosol comprising at least one foaming agent and oxygen/air and configured for use in a ventilation system or other breathing system adapted to treat an individual having respiratory distress and/or respiratory symptoms.

Yet another aspect of the invention relates to a ventilation system or other breathing system configured to administer at least one foaming agent with oxygen/air, and preferably further configured to apply energy to a portion of the lower respiratory system and/or preferably configured to provide suction to remove fluid/foam/bubbles from treatment area, to treat an individual having respiratory distress.

The foregoing has outlined some of the aspects of the present invention. These aspects should be construed strictly as illustrative of some of the more prominent features and applications of the invention, rather than as limitations on the invention. Many other beneficial results can be obtained by modifying the embodiments within the scope of the invention. Accordingly, for other objects and a full understanding of the invention, refer to the summary of the invention, the detailed description describing the preferred embodiment in addition to the scope of the invention defined by the claims and any accompanying drawings. The unique features characteristic of this invention and operation will be understood more easily with the description and drawings. It is to be understood that any drawings are for illustration and description only and do not define the limits of the invention.

DETAILED DESCRIPTION OF PREFERRED EMBODIMENTS

In the following description, for purposes of explanation, specific details are set forth in order to provide a thorough understanding of different aspects of the present invention. It will be evident, however, to one skilled in the art that the present invention as defined by the claims may include some or all of the features or embodiments herein described and may further include obvious modifications and equivalents of the features and concepts described herein.

DEFINITIONS

As used herein, the singular forms "a," "an" and "the" include plural referents unless the context clearly dictates otherwise. Thus, for example, reference to a "molecule" (or to a "method step") includes aspects having two or more such molecules (or aspects including two or more method steps) unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect and "about" is utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue. It will be further understood that the endpoints of each of the ranges are significant both in relation to the other endpoint, and independently of the other endpoint.

Terms used herein, such as "aspect" or "embodiment" or "exemplary" or "exemplified," are not meant to show preference, but rather to explain that the aspect discussed thereafter is merely one example of the aspect presented.

Additionally, as used herein, relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

The term "breathing system" as used herein includes ventilator systems, non-rebreather mask systems, high-flow nasal cannula, continuous positive airway pressure (CPAP) and other system for providing oxygen to an individual.

The term "effective amount" (and "amount effective") refers to the amount of a therapy (e.g., process step, process parameter(s), a prophylactic or therapeutic agent, composition, formulation, treatment time, etc.), which is sufficient to reduce the severity, and/or duration of an illness, disease or infection, ameliorate one or more symptoms thereof, prevent the advancement of an illness, disease or infection, or cause regression of an illness, disease or infection, or which is sufficient to result in the prevention of the development, recurrence, onset, or progression of an illness, disease or infection or one or more symptoms thereof, or enhance or improve the prophylactic and/or therapeutic effect(s) of another therapy (e.g., another therapeutic agent).

As used herein, the terms "optional" or "optionally" mean that the subsequently described event or circumstance may or may not occur or the component might be omitted, and that the description includes instances where said event or circumstance occurs and instances where it does not or when the component is present or not.

The term "pharmaceutically acceptable" means being approved by a regulatory agency of the Federal or a state government or listed in the U.S. Pharmacopia, European Pharmacopia or other generally recognized pharmacopia for use in animals, and more particularly in humans.

The term "pharmaceutical drug" as used herein refers to a medication or medicine used to cause a change in an organism's physiology or psychology when consumed or administered, or otherwise intended to produce a biological effect.

The terms "prevent", "preventing", and "prevention" refer to the prevention or reduction of the recurrence, onset, development or progression of an infection, or the prevention or reduction of the severity and/or duration of an infection, disease and/or illness or one or more symptoms thereof.

The terms "prophylactic agent" and "prophylactic agents" refer to any agent(s) which can be used in the prevention of an infection, disease and/or illness and/or one or more symptoms thereof.

The term "prophylactically effective amount" refers to the amount of a composition (e.g., liquid or aerosol formulation of the invention) which is sufficient to result in the prevention of the development, recurrence, onset or progression of an infection, disease and/or illness.

A used herein, a "protocol" includes dosing schedules and dosing regimens. The protocols herein are methods of use and include prophylactic and therapeutic protocols.

The term "respirable" as used herein refers to compounds, molecules, dry particles or dry powders that may enter into the respiratory tract (e.g., pulmonary delivery) in a subject by inhalation.

The term "superposition" as used herein refers to when at least two waves occupy the same point (e.g., the "superposition" wave at such point is found by adding the two amplitudes of the waves).

The term "surface energy" is used herein to refer to the work per area done by a force that creates a surface. Surfaces have energy associated with them because of the work needed to form a surface.

The terms "therapies" and "therapy" can refer to any protocol(s), method(s) and/or agent(s) that can be used in the prevention, treatment, management or amelioration of an infection, disease and/or illness and/or one or more symptoms thereof. In certain embodiments, the terms "therapy" and "therapies" refer to biological therapy, and/or other therapies useful for the treatment of an infection, disease and/or illness known to skilled medical personnel.

The terms "treat", "treating" and "treatment" refer to the reduction or amelioration of the progression, severity, and/or duration of an infection, disease and/or illness and/or reduces or ameliorates one or more symptoms of an infection, disease and/or illness. In specific embodiments, such terms refer to the reduction or inhibition of the replication of a virus, the inhibition or reduction in the spread of a virus (e.g., to other tissues or subjects), the inhibition or reduction of infection of a cell with a virus, and/or the amelioration of one or more symptoms associated with a virus infection, disease and/or illness.

As used herein, the term "surfactant" refers to organic substances having amphipathic structures; namely, they are composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants.

The invention relates to methods for treating individuals having respiratory distress and compositions for use in the same.

One aspect of the invention relates to method of treating an individual having at least one lower respiratory system region with at least one respiratory failure symptom, the method comprising administrating at least one foaming agent to the at least one lower respiratory system region. Preferably, the method further comprises applying external energy (e.g., vibrational energy) to the at least one lower respiratory system region.

One embodiment of the invention relates to method of treating an individual having at least one lower respiratory system region with at least one respiratory failure symptom, the method comprising administrating a prophylactically effective amount of at least one foaming agent to the at least one lower respiratory system region, preferably to an individual exhibiting one or more ARDS symptoms.

Another aspect of the invention relates to method of treating an individual having at least one lower respiratory system region with at least one respiratory failure symptom, the method comprising:
(a) administrating at least one foaming agent to the at least one lower respiratory system region; and
(b) applying external energy to the at least one lower respiratory system region including to at least one alveolus in an effective amount and for an effective time period to reduce the at least one respiratory failure symptom.

According to one embodiment of the invention relates to a method of treating an individual having at least one lower respiratory system region with ARDS symptoms, the method comprising:
(a) administrating at least one foaming agent to the at least one lower respiratory system region; and
(b) applying external energy to the at least one lower respiratory system region including the at least one alveolus in an effective amount and for an effective time period to reduce the ARDS symptoms.

Another embodiment of the invention relates to a method of treating an individual having at least one lower respiratory system region with ARDS and/or other respiratory failure symptoms, the method comprising applying external energy to the at least one lower respiratory system region including the at least one alveolus in an effective amount and for an effective time period to reduce the ARDS and/or other respiratory failure symptoms.

According to another embodiment, the invention relates to a method of treating an individual having at least one lower respiratory system region with ARDS and/or other respiratory failure symptoms, the method comprising administrating at least one foaming agent to the at least one lower respiratory system region including the at least one alveolus in an effective amount and for an effective time period to reduce the ARDS and/or other respiratory failure symptoms.

Preferably, the individual has at least one lower respiratory system region including at least one alveolus containing excess fluid in amounts sufficient to inhibit gas exchange.

Preferably, the individual has at least one lower respiratory system region including at least one alveolus having excess alveolar edema fluid.

According to preferred embodiments, the method treats individuals with at least one respiratory failure symptom is caused by a virus or viral infection (e.g., SARS, COVID-19, MERS).

According to other preferred embodiments, the methods and systems are configured to treat individuals with at least one other respiratory failure symptom resulting in excess mucus or other fluids in the lungs or regions of the lungs (e.g., cystic fibrosis, chronic obstructive pulmonary disease (COPD), asthma, or other chronic mucus hypersecretion or chronic sputum production).

According to one further preferred embodiment, at least one mucus thinner (e.g., hypertonic saline, dornase alfa, etc.) is administered (i) prior to the administration of the at least one foaming agent and/or application of external energy and/or (ii) during the administration of the at least one foaming agent and/or application of external energy. Preferably, the external energy is applied using a vibration vest.

According to preferred embodiments, the method treats individuals with normal or substantially normal respiratory compliance.

According to preferred embodiments, the individual has acute respiratory distress syndrome and the at least one respiratory failure symptom is a reduction in alveolar fluid clearance.

According to preferred embodiments of the invention, the methods are configured for the treatment of a virus or one or more symptom(s) caused or resulting from the virus. Non-limiting examples of an industrially relevant virus include a retrovirus, a herpesvirus, a flavivirus, a poxvirus, a hepadnavirus, a hepatitis virus, an orthomyxovirus, a paramyxovirus, a rhabdovirus, or a togavirus. In any variation of the invention, a virus is selected from the group consisting of an adenovirus, African swine fever-line virus, arenavirus, arterivirus, astrovirus, baculovirus, badnavirus, barnavirus, birnavirus, bromovirus, bunyavirus, calicivirus, capillovirus, carlavirus, caulimovirus, circovirus, closterovirus, comovirus, coronavirus (including SARS and COVID-19), cotricovirus, cystovirus, deltavirus, dianthovirus, enamovirus, filovirus, flavivirus, furovirus, fusellovirus, geminivirus, hepadnavirus, herpesvirus, hordeivirus, hypovirus, ideaovirus, inovirus, iridovirus, levivirus, lipothrixvirus, luteovirus, machlomovirus, marafivovirus, microvirus, myovirus, necrovirus, nodavirus, orthomyxovirus, papovavirus, paramyxovirus, partitivirus, parvovirus, phycodnavirus, picornavirus, plamavirus, podovirus, polydnavirus, potexvirus, potyvirus, poxvirus, reovirus, retrovirus, rhabdovirus, rhizidiovirus, sequevirus, siphovirus, sobemovirus, tectivirus, tenuivirus, tetravirus, tobamavirus, tobravirus, togavirus, tombusvirus, totivirus, trichovirus, tymovirus, and umbravirus.

According to alternative preferred embodiments of the invention, the methods are configured for the treatment of bacterial or other pathogen infections, smoke-related lung damage (including e-cigarette ARDS-like symptoms) and environmental exposures resulting in similar lung symptoms (e.g., high altitudes, chemical exposure, etc.) or other respiratory failure symptom resulting in excess mucus or other fluids in the lungs or regions of the lungs (e.g., cystic fibrosis, chronic obstructive pulmonary disease (COPD), asthma, or other chronic mucus hypersecretion or chronic sputum production).

One aspect of the invention relates to methods of generating at least one bubble preferably from the excess fluid (e.g., edema fluid), within at least one alveolus and/or from the excess mucus within the lung. Preferably, the method comprises applying energy (preferably external energy) in an amount sufficient to generate a plurality of bubbles (more preferably a network of bubbles) within at least one alveolus (or with a lung or a region of a lung).

Preferably, the method comprises applying external energy in an amount sufficient to generate a foam (preferably from the excess fluid) within at least one alveolus and/or excess mucus within the lung or region of the lung.

Preferably, the method comprises administering an effective amount of foaming agent(s) and/or applying an effective amount of energy to generate or produce a plurality of bubbles and/or a network of bubbles or foam.

Preferably, the method comprises administering an effective amount of foaming agent(s) and/or applying an effective amount of energy to treat the illness/disease/infection and/or reduce one or more symptoms caused by the illness/disease/infection (which includes damage caused by other treatments of the illness/disease/infection).

Preferably, the method comprises administering an effective amount of foaming agent(s) and/or applying an effective amount of energy to allow for increased oxygen/carbon dioxide exchange.

Preferably, the method comprises administering an effective amount of foaming agent(s) and/or applying an effective amount of energy to allow for an effective amount of liquid within an alveoli to be removed from the alveoli and/or an effective amount of mucus within the lung to be removed.

Preferably, the method comprises administering an effective amount of foaming agent(s) and/or applying an effective amount of energy to reduce the amount of liquid within an alveoli and/or the amount of mucus to within the lung.

The methods of the invention preferably include the administration of at least one foaming agent to the at least one lower respiratory system region, preferably by a breathing system. Often, individuals with respiratory illness such as ARDS are treated with traditional mechanical ventilation or other breathing system to provide supplemental oxygen to the individual. Such ventilation and other systems and methods are well known in the art.

According to preferred embodiments, the at least one foaming agent is delivered using a ventilator or other breathing system. Methods of administering drugs or biological agents using ventilation systems are well known in the art. See, for example, U.S. Pat. No. 7,909,031 to Shaffer; U.S. Pat. No. 9,358,358 to Wonka et al.; U.S. Pat. No. 5,707,352 to Sekins et al.; U.S. Pat. No. 6,112,744 to Hognelid; U.S. Pat. No. 9,032,951 to Finlay et al.; U.S. Pat. No. 8,931,478 to Dunsmore et al.; U.S. Pat. No. 8,910,627 to Iwatschenko et al.; U.S. Pat. No. 8,733,348 to Korneff; U.S. Pat. No. 8,720,435 to Gallem et al.; U.S. Pat. No. 8,397,716 to Calluaud et al.; and U.S. Pat. No. 8,616,195 to Power et al., each describe methods and systems for delivering biological agents and/or drugs and each is hereby incorporated by reference in its entirety. Nebulizers for ventilation machines are well known in the prior art. For example, WO 2005/048982 A2, herein incorporated by reference in its entirety, discloses a nebulizer comprising a body having a first connection that comprises two connecting pieces for connecting the nebulizer to an air supply line and an air exhaust line of the ventilation device.

As is known to those skilled in the art, a bronchial passageway defines an internal lumen through which fluid can flow to and from a lung. The diameter of the internal lumen for a specific bronchial passageway can vary based on the bronchial passageway's location in the bronchial tree (such as whether the bronchial passageway is a lobar bronchus or a segmental bronchus) and can also vary from patient to patient. However, the internal diameter of a bronchial passageway is generally in the range of 3 millimeters (mm) to 10 mm, although the internal diameter of a bronchial passageway can be outside of this range. For example, a bronchial passageway can have an internal diameter of well below 1 mm at locations deep within the lung.

According to preferred embodiments of the invention, the method uses a ventilator or other breathing system and the external energy comprises one or more variations in flow rate, flow volume, flow composition, pressure and/or temperature of the gas/aerosol/liquid administered by the system. Preferably, the variation occurs in an effective amount to generate one or more bubbles and/or foam.

Preferably, the one or more variations are greater than 1%, more preferably greater than 5%, more preferably greater than 10%, even more preferably greater than 15%, even more preferably greater than 20%, even more preferably greater than 25%, even more preferably greater than 30%, even more preferably greater than 35%, even more preferably greater than 50%, even more preferably greater than 55%, even more preferably greater than 60%, even more preferably greater than 65%, and even more preferably greater than 75%.

Preferably, the variation occurs within an effective amount of time to generate one or more bubbles and/or foam within a lung or region of a lung. Preferably, the time is less than 5 seconds, more preferably less than 2 seconds, more preferably less than 1 second, more preferably less than 0.5 second, even more preferably less than 0.1 second, even more preferably less than 0.01 seconds, even more preferably less than 0.001 seconds, and even more preferably less than 0.0005 seconds. That is, the variation change is preferably quick enough to result in sufficient energy within the aveoli to generate one or more bubbles and/or foam (e.g., generate mixing or mixing energy within the aveoli).

Methods of using ventilators and other breathing systems to support patients with respiratory illness/symptoms are well known (including ventilator systems/methods adapted to administer drugs, etc.) and can be applied to the methods described herein.

Preferred methods of treatment can be summarized according to the following steps (some of the steps are optional and the steps are not necessarily performed in the order listed below). The preferred steps include:
- (a) identifying a targeted lung region and determining a target location in bronchial passageway(s) to which the administration of the foaming agent and application of energy will be deployed;
- (b) positioning a delivery catheter within the bronchial passageway so that the breathing system flow (e.g., ventilator flow) is positioned at the target location in the bronchial passageway;
- (c) administering at least one foaming agent to the target location in the bronchial passageway; and
- (d) applying energy to the targeted lung region and/or, preferably in an amount sufficient for bubble/foam generation to occur in the targeted lung region, and, optionally, removing the bubble/foam/liquid available to suction or otherwise remove.

According to step (a), a physician or technician evaluates and/or diagnoses the diseased area of a patient's lung to determine the targeted lung region and then determines the bronchial passageway(s) that provide airflow to the targeted lung region. Based on this, one or more target locations of bronchial passageways can be determined to which the method can be deployed.

The breathing system (preferably ventilation system) may include additional components and features including one or more of the following:
- (1) A suction catheter for aspirating air or fluid from the target region.
- (2) A long, thin suction catheter that could be snaked into very distal portions of the isolated lung region for aspirating fluid or air in the distal portions of the isolated lung regions.
- (3) A short tube to allow free fluid communication between the occluded region of a bronchial passageway distal of the target region and the region of the bronchial passageway proximal of the target region.
- (4) A tube or other short structure with a one-way valve mounted inside the catheter or distal components to allow fluid to be expelled from the isolated distal lung region (either during normal exhalation or during a procedure that forces fluid/foam/bubbles from the isolated, distal lung region) and to prevent fluid from entering or re-entering the target region or other lung region.
- (5) A catheter with a one-way valve mounted at the tip to allow fluid/bubbles/foam to be expelled from the isolated, distal lung region (either during normal exhalation or during a procedure that forces fluid/bubbles/form from the distal lung segment) and to prevent fluid/bubbles/foam from entering the lung segment.
- (6) A catheter for instilling additional foaming agent(s), a therapeutic agent, such as antibiotics or other medication, into the region of the bronchial passageway or lung distal to the device that has been implanted in the bronchial passageway.
- (7) A catheter for passing brachytherapy sources into the bronchial passageway for therapeutic reasons, such as to stop mucus production, kill a pneumonia infection, etc. The brachytherapy source can be configured to emit either Gamma or Beta radiation.
- (8) A catheter with a semi-permeable distal aspect that circulates a nitrogen-solvent fluid, which absorbs through osmosis nitrogen trapped in the lung region distal.

Typically, the ventilator settings, for example, are continually changed during treatment of a patient. These settings include percent of oxygen going through to the patient's lungs (the air we breathe is about 20% oxygen, but ventilators can give up to 100% oxygen if needed). It also includes how much volume of air is administered, often depending on the size of the patient, at what pressure this oxygen is administered, at what rate, and at what flow. In addition, variables such as patient-initiated ventilation rate versus rate wholly run by the machine can fluctuate, depending on the patient's lung function and whether or not there is any residual ability for the patient to generate breaths on his or her own. These settings are continually assessed by highly trained specialists, who are making changes to medications, ventilatory settings, and patient positioning (on the back or on the belly—supine or prone) based on the minute-to-minute clinical status of the patient. Several of the terms and parameters used with ventilation systems include:

Respiratory rate (RR)—The number of breaths taken in one minute.

Tidal Volume (VT)—The volume of air (ml) taken in a single breath. In general, this ranges from 4-8 ml/kg (ideal body weight). Example for a 60 kg patient would be volumes of 240-480 ml per breath.

Airway Pressure—The amount of pressure (cm $H_2O$) felt pushing outward on the airways. The pressure in the airway changes during a breath. The highest pressure is called the peak pressure, the sustained pressure during inhalation is the plateau pressure. During normal exhalation the pressure drops to near zero.

Positive End-Expiratory Pressure (PEEP)—An externally applied pressure to the airway and lungs to help push small airways and alveoli open. Often improves oxygenation in diseased lungs.

Minute Ventilation (MV)—The total volume of air moved in 1 minute (MV=RR*VT).

Management concept: If airway pressure gets too high, lowering the tidal volume and increasing the respiratory rate can keep pressure low and deliver the same amount of air.

Compliance—How elastic the lung is. It is defined as how much the lung changes volume (stretches) as pressure is changed. A car tire has a low compliance, while a balloon has high compliance.

Resistance—How hard it is for air to flow into or out of the lungs. This can be made worse in diseases like asthma or chronic obstructive pulmonary disease (COPD) when the airway is decreased in size.

Inspiratory to Expiratory (I:E) ratio—A comparison of the time spent during inspiration to the time required for exhalation. In a normal patient this is usually 1:2 but can vary from 2:1 to 1:4 depending on patient pathology and ventilation parameters sought.

Ventilation breathing modes: A person who is getting assistance breathing from a ventilator may need different amounts of help. These are given the terms—support, assist, and control:

Support: Ventilator gives some, but not all help once it detects an attempt to breathe. (If the patient does not have enough effort the patient could be under ventilated)

Assist: Ventilator waits until it senses an attempt to breathe (slight inspiratory effort) and then will deliver the full breath specified (volume or duration) and usually at a minimum set respiratory rate.

Control: In this mode, the ventilator does all of the work, delivering the full volume or duration of breath even if no effort is made by the patient.

Breath delivery types: The two external breathing types are pressure support and volume support.

Pressure support: A fixed pressure (cmH2O) is provided to 'push' air into the lungs. The actual delivered volume may vary depending on the physiology of the lungs (compliance and resistance).

Volume Support: A fixed volume (ml) of air is provided to the lung with an adjustment (increase or decrease) in pressure to achieve this.

According to preferred embodiments, one or more of the breathing system (preferably ventilation system) parameters described above are varied or adjusted or stop/restarted to generate sufficient energy within the target region to generate one or more bubbles and/or foam. For example, the Minute Ventilation (MV) is varied in an effective amount to generate sufficient energy within the target region to generate one or more bubbles and/or foam and/or reduce one or more symptoms. For example, typical MW may range from 70-120 mL/kg/min PBW and the ventilation system MW will vary from, for example, 80 mL/kg/min PBW to 100 mL/kg/min PBW and return to 80 mL/kg/min PBW, preferably repeatedly. Alternately, or in combination, the pressure (peak airway pressure (PIP), plateau pressure (Pplt), PEEP and/or CPAP) are varied to generate the energy.

Preferably, the one or more of the parameters above are varied greater than 1%, more preferably greater than 5%, more preferably greater than 10%, even more preferably greater than 15%, even more preferably greater than 20%, even more preferably greater than 25%, even more preferably greater than 30%, even more preferably greater than 35%, even more preferably greater than 50%, even more preferably greater than 55%, even more preferably greater than 60%, even more preferably greater than 65%, and even more preferably greater than 75%.

Preferably, the variation occurs within an effective amount of time to generate one or more bubbles and/or foam and/or in a prophylactically effective amount (e.g., to improve one or more symptoms). Preferably, the time is less than 5 seconds, more preferably less than 2 seconds, more preferably less than 1 second, more preferably less than 0.5 second, even more preferably less than 0.1 second, even more preferably less than 0.01 seconds, even more preferably less than 0.001 seconds, and even more preferably less than 0.0005 seconds. That is, the variation change is preferably quick enough to result in sufficient energy within the aveoli to generate one or more bubbles and/or foam and/or in a prophylactically effective amount (e.g., to improve one or more symptoms).

According to preferred embodiments, PEEP is maintained at approximately 5 to keep the alveoli open to allow any bubbles/foam created to continue to form and/or expand (e.g., to prevent the alveoli from closing to reduce risk of foam/bubble collapse after each breath).

According to one embodiment, the at least one foaming agent is delivered as an aerosol. Preferably, the method further comprises generating an aerosol comprising the at least one foaming agent and/or aerosolizing a formulation or composition comprising the foaming agents.

According to another embodiment, the at least one foaming agent is delivered in a liquid (preferably saline solution).

According to preferred embodiments, the method further comprises administering cholesterol. See, WO 2006071796, herein incorporated by reference in its entirety.

According to preferred embodiments, the method further comprising administering sodium.

According to preferred embodiments, the method further comprising administering mucus thinner (e.g., hypertonic saline, dornase alfa, etc.)

Preferred embodiments relate to the treatment of an individual or patient who has been intubated. Preferably, the individual is at least five years old, more preferably at least 10 years old, even more preferably at least 16 years old, even more preferably at least 25 years old, even more preferably at least 40 years old and most preferred over 60 years old.

Preferably, the methods and/or systems described herein are administered to individuals preferably excluding newborns or infants.

Preferably, the foaming agent is aspirated into the lungs during the breathing and/or ventilation maneuvers while simultaneously flowing and spreading across of the lung surfaces.

Preferably, the at least one foaming agent is effectively delivered as an aerosol in sufficient quantity and effective amount to exert a therapeutic response and/or in a prophylactically effective amount (e.g., to improve one or more symptoms).

According to preferred embodiments, to reduce the risks to the individual, the method of administration is directly focused on a partial portion of a lung while the other portion is not directly administered. Preferably, the method is performed one lung at a time, more preferably one portion of a lung (e.g., a lobe) at a time. See, for example, U.S. Pat. No. 8,955,518 to Wondka; U.S. Pat. No. 7,011,094 to Rapacki et al.; U.S. Pat. No. 7,588,033 to Wondka et al.; U.S. Pat. No. 8,876,791 to Wondka et al.; U.S. Pat. No. 10,441,735 to Zhou; and WO 2013/188845 to Hoftman et al., each of which describes such methods and systems and each is hereby incorporated by reference in its entirety.

Preferably, the at least one foaming agent is administered in a carrier (gas/liquid/aerosol) and the administrating flow rate is preferably varied (preferably by the percentages and/or time periods described above). For example, the gas and/or aerosol and/or liquid (e.g., saline solution with foaming agent(s)) is pulsed (on/off, high/low, combinations) and/or used alternatively to generate mixing/energy.

For example, according to one preferred embodiment, the ventilation system first administers gas, followed by a burst or portion of aerosol (including a foaming agent), followed by gas, aerosol, etc. For example, one or more aerosol generators are incorporated into the ventilation system and can be turned on/off or varied to generate variations in flow, composition and the like. See, for example, U.S. Pat. No.

8,800,557 to Andreiux and U.S. Pat. No. 7,011,094 to Rapacki et al., which disclose methods and systems for regulating fluid flow to and from a region of a patient's lung, such as to achieve desired flow dynamic to a lung region during respiration, such methods and systems disclosure, each herein incorporated by reference in its entirety.

According to preferred embodiments, the ventilation system alternates between air/O2 and either liquid or aerosol (preferably containing foaming agent). For example, an aerosol to administered in bursts to generate the energy (e.g., mixing).

A variety of different energies can be applied to the lung region to create an effective amount of energy to generate bubbles and/or foam and/or treat the illness, disease, infection, lung damage, and/or symptoms associated with the same.

The external energy can include on or more of the following: (i) acoustic/sound waves/ultrasound; (ii) vibrational energy; (iii) magnetic waves; (iv) electromagnetic waves (e.g., light, radiation); (v) gas/pressure/flow rate variations; (vi) temperature variations; and/or (v) chemical energy (e.g., chemical additives to generate gas bubbles).

According to preferred embodiments, two or more forms of energy are applied (e.g., vibrational energy and varying flow rate of breathing system) to the patient.

According to one embodiment, the external energy is selected from the group consisting of ultrasound, microwave radiofrequency energy, magnetic induction oscillating energy, and light energy.

According to another embodiment, the external energy comprises continuous wave ultrasound energy.

According to another embodiment, the external energy is selected from the group consisting of amplitude and frequency modulated pulses.

According to another embodiment, the external energy is applied as a pulse.

According to another embodiment, the external energy is applied externally to the patient.

According to another embodiment, the external energy is applied endoscopically to the patient.

Many forms of energy involve waves. Superposition occurs when two waves occupy the same point (the wave at this point is found by adding the two amplitudes of the waves). Superposition can be achieved with one or more of the energy sources described herein including sound waves, vibrational waves, light waves, etc.

Waves are most commonly described by variations in some parameter through space and time—height in a water wave, pressure in a sound wave, or the electromagnetic field in a light wave. The value of this parameter is called the amplitude of the wave; the wave itself is a function specifying the amplitude at each point. When two or more waves arrive at the same point, they superimpose themselves onto one another. More specifically, the disturbances of waves are superimposed when they come together (a phenomenon called superposition). Each disturbance corresponds to a force, or amplitude (and the forces add). If the disturbances are along the same line, the resulting wave is a simple addition of the disturbances of the individual waves. That is, their amplitudes add. According to the invention, preferred embodiments relate to the use of two or more sources of energy waves positioned around the target region and configured to direct each energy wave to intersect within the target region to enhance the energy impact delivered to the target region.

Another embodiment relates to methods wherein the external energy is at least one sound wave.

According to preferred embodiments, the external energy comprises a first sound wave and a second sound wave, wherein the first sound wave is not parallel to the second sound wave and the first sound wave and the second sound wave intersect (or substantially intersect) within the patient, preferably at least one lower respiratory system region.

According to preferred embodiments, the external energy comprises a plurality of sound waves that intersect within the patient, preferably the at least one lower respiratory system region. Preferably, the plurality of waves is configured to result in superposition or substantial superposition of the plurality of sound waves within the patient, preferably the at least one lower respiratory system region.

Another alternate embodiment of the invention relates to a method of treating a patient comprising applying a plurality of sound waves that intersect within the patient, preferably the at least one lower respiratory system region or other region within patient with symptom(s). Preferably, the plurality of waves is configured to result in superposition or substantial superposition of the plurality of sound waves within the patient, preferably the at least one lower respiratory system region or other region with symptom(s).

According to preferred embodiments, the external energy comprises a plurality of sound waves positioned around the patient, preferably the at least one lower respiratory system region and configured to intersect (or substantially intersect) within the patient, preferably the at least one lower respiratory system region.

Preferably, the plurality of sound waves is pulsed over time.

Preferably, the plurality of sound waves is independently pulsed over time. According to alternative embodiments, the plurality of sound waves is pulsed over time not in sync.

Although the frequency of the sound wave(s) can vary depending on the number of sound generators, patient size, fluid within the aveoli, lung compliance and other factors, the frequency of the sound waves is preferably greater than 20,000 Hz, more preferably greater than 22,000 Hz, even more preferably greater than 23,000 Hz, even more preferably greater than 24,000 Hz.

Although the frequency of the sound wave(s) can vary depending on the number of sound generators, patient size, fluid within the aveoli, lung compliance and other factors, the sound decibel of the sound wave(s) is preferably greater than 10 decibels, more preferably greater than 15 decibels, even more preferably greater than 20 decibels, even more preferably greater than 25 decibels, even more preferably greater than 30 decibels, even more preferably greater than 35 decibels, even more preferably greater than 40 decibels, even more preferably greater than 50 decibels, even more preferably greater than 60 decibels, even more preferably greater than 70 decibels.

According to preferred embodiments, the external energy comprises acoustic mixing.

According to preferred embodiments, the external energy includes acoustics.

According to preferred embodiments, the external energy comprises ultrasound.

According to preferred embodiments, the external energy comprises sonication.

According to preferred embodiments, the application of the external energy comprises generating a first sound wave and a second sound wave and directing the first sound wave and the second sound wave to the patient, preferably to the at least one lower respiratory system region including to at least one alveolus.

Another embodiment relates to methods wherein the external energy comprises vibrations.

Preferably, the external comprises two or more sources of vibrations (e.g., a first vibrating plate adjacent to back of patient and a second adjacent to the side of the patient).

According to preferred embodiments, the method comprises the application of vibration from a vibration vest fitted on the patient, preferably a vest configured for vibration therapy. See, for example, U.S. Pat. No. 8,443,796 to Hughes; US 2017/0112707 to Huster et al.; U.S. Pat. No. 7,931,607 to Biondo et al., and U.S. Pat. No. 6,676,614 to Hansen, each hereby incorporated by reference in its entirety. Vibrating mats and/or plates and/or pads may also be used. A vibrating mouthpiece may also be used. See, U.S. Pat. No. 8,443,796 to Hughes, hereby incorporated by reference in its entirety.

According to preferred embodiments, at least one vibration source is used to provide the energy to the target area, more preferably at least two vibration sources to provide two waves of vibrational energy to the target area, more preferably at least three vibration sources, and even more preferably at least four vibration sources.

Another embodiment of the invention relates to methods wherein the external energy comprises electromagnetic radiation.

According to preferred embodiments, the external energy comprises at least one radiation wave directed at least one lower respiratory system region.

According to preferred embodiments, the external energy comprises a first radiation wave and a second radiation wave, wherein the first radiation wave is not parallel to the second radiation wave and the first radiation wave and the second radiation wave intersect within the patient, preferably the at least one lower respiratory system region.

According to preferred embodiments, the external energy comprises a plurality of radiation waves that intersect within the patient, preferably the at least one lower respiratory system region. Preferably, the plurality of radiation waves is configured to result in superposition of the plurality of radiation waves within the patient, preferably the at least one lower respiratory system region.

According to preferred embodiments, the external energy comprises a plurality of radiation waves positioned around the patient, preferably the at least one lower respiratory system region and configured to intersect within the patient, preferably the at least one lower respiratory system region.

Preferably, the plurality of radiation waves is pulsed over time.

Preferably, the plurality of radiation waves is independently pulsed over time.

According to another embodiment, the external energy comprises at least one proton beam configured to reach the proton Bragg Peak within the at least one lower respiratory system region. The major advantage of proton therapy treatment over standard radiation therapy is that protons slowly deposit their energy as they travel towards the cancerous tumor, for example, and then due to a unique physical characteristic called the Bragg Peak, deposit the majority of the radiation dose directly in the tumor and travel no further through the body. This results in less healthy tissues and organs receiving unnecessary radiation thereby reducing unwanted complications and side effects. Standard radiation therapy utilizes x-rays which deposits the majority of the radiation dose immediately upon entering the body while traveling to the tumor. Unlike protons, after depositing the radiation dose in the tumor the x-rays continue traveling through the body until exiting out the other side resulting in the delivery of unnecessary radiation to healthy tissues and organs. Simply put, protons stop after depositing the radiation dose in the tumor, x-rays do not.

Preferably, the external energy comprises a first proton beam and a second proton beam, wherein the first proton beam is not parallel to the proton beam and the first proton beam and the second proton beam intersect within the at least one lower respiratory system region. Preferably, the external energy comprises a plurality of proton beams that intersect within the at least one lower respiratory system region. Preferably, the external energy comprises a plurality of proton beams positioned around the at least one lower respiratory system region and configured to intersect within the at least one lower respiratory system region. Preferably, the plurality of proton beams is pulsed over time. Preferably, the plurality of proton beams is independently pulsed over time.

According to alternative embodiments, the external energy comprises at least focused high-energy radiation beam, preferably a plurality of focused high-energy radiation beams.

According to another embodiment of the invention, the external energy comprises magnetic mixing.

According to another embodiment of the invention, the external energy comprises magnetically assisted impaction mixing.

According to another embodiment of the invention, the external energy comprises applying an oscillating magnetic field to the target region of the lung to cause mixing.

Preferably, the method further comprises administering at least one magnetic nanoparticle and/or magnetic complex/molecule.

According to another embodiment of the invention, the external energy comprises the generation or formation of gas bubbles within the alveoli to generate bubbles/foam and/or network of bubbles from the liquid. Preferably, one or more compounds or molecules are administrated that result in formation of gas or other chemical energy to facilitate generation of bubbles/foam from the liquid in the alveoli.

One preferred embodiment comprises administering one or more molecules configured to generate energy sufficient to generate foam within the one or more aveolus/aveoli containing excess fluid and/or within the lung or region of lung including excess mucus.

One aspect of the invention relates to methods comprising administrating one or more molecules and/or compounds and/or gases and/or formulations that facilitate the formation and/or generation and/or product of bubbles or foam within the aveoli within the lung or region of lung including excess mucus.

According to preferred embodiments, the at least one foaming agent comprises one or more surfactants.

Preferably, the at least one foaming agent comprises one or more natural surfactants.

Alternatively, the at least one foaming agent comprises one or more synthetic surfactants.

Preferably, the at least one foaming agent comprises one or more lung surfactants and/or one or more pulmonary surfactants.

Currently, at least three classes of lung surfactant replacements are used for treatment of different respiratory diseases: (1) "natural", (2) "synthetic" and (3) "biomimetic". See, for example, WO2006071796 to Rairkar, particularly the surfactants discussed paragraph 0045, hereby incorporated by reference in its entirety.

According to preferred embodiments, the at least one foaming agent comprises dipalmitoylphosphatidylcholine (DPPC).

According to preferred embodiments, the at least one foaming agent comprises Tween biocompatible surfactant, preferably polyethylene sorbitol ester (e.g., Tween 80) and/or polyoxyethylene sorbitol esteris (e.g., Tween 20). For example, it is known that 0.01% Tween 80 has little effect on most physiological functions of any cells or tissues, thus being useful as a biocompatible surfactant. Preferably, the therapeutic composition for administration comprises a dispersant (e.g., one or more surfactants such Tween 20, Tween 80, or the like, preferably in low levels (e.g., preferably less than 1 wt %, more preferably less than 0.1 wt %, even more preferably less than 0.05 wt %, and most preferred about 0.01 wt %)).

According to preferred embodiments, the at least one foaming agent comprises decyl glucoside.

One embodiment of the invention relates to method of treating an individual having at least one lower respiratory system region with at least one respiratory failure symptom, the method comprising administrating an prophylactically effective amount of both (i) at least one foaming agent and (ii) polyethylene sorbitol ester, polyoxyethylene sorbitol esteris and/or decyl glucoside, to the at least one lower respiratory system region, preferably to an individual exhibiting one or more ARDS symptoms.

According to additional preferred embodiments, the at least one forming agent comprises two or more surfactants selected from: (a) one or more natural surfactants and/or (b) one or more synthetic surfactants.

According to additional preferred embodiments, the at least one forming agent comprises dipalmitoylphosphatidylcholine (DPPC) and one or more synthetic surfactants.

According to additional preferred embodiments, the at least one forming agent comprises decyl glucoside and one or more synthetic surfactants.

According to additional preferred embodiments, the at least one forming agent comprises dipalmitoylphosphatidylcholine (DPPC), decyl glucoside and one or more synthetic surfactants.

According to further preferred embodiments, the method further comprises administering Na+ to the at least one lower respiratory system region.

According to further preferred embodiments, the method further comprises administering at least one wetting agent to the at least one lower respiratory system region. The term "wetting agent" as used herein means a material that reduces the surface tension of a liquid and therefore increases its adhesion to a solid surface.

In particularly preferred embodiments of the invention, the surfactant does not comprise or form octylphenol. In particularly preferred embodiments, the surfactant does not comprise or form peroxide.

In preferred embodiments of the invention, upon disposal the surfactant's Predicted Environmental Concentration (PEC) in a receiving water body resulting from use of the surfactant is below the Predicted No-Effect Concentration (PNEC) of the surfactant. In further embodiments, the PEC is lower than the PNEC.

In some preferred embodiments of the invention, the environmentally compatible surfactant comprises an alkyl glucoside. In further preferred embodiments, the alkyl glucoside is a decyl glucoside. In other embodiments, the environmentally compatible surfactant is an alcohol ethoxylate. In yet other embodiments, the environmentally compatible surfactant is an alkyl polyethylene glycol ether. In some embodiments, the environmentally compatible surfactant has a CAS registry number of CAS 9005-64-5, CAS 9005-65-6. CAS 126-43-8, 68515-73-1, CAS 58846-77-8, CAS 59122-55-3, CAS 110615-47-9, CAS 29836-26-8, CAS 64366-70-7, CAS 68937-66-6, CAS 69227-22-1, CAS 25322-68-3, CAS 27252-75-1, CAS 4292-10-8, CAS 132778-08-6, CAS 110615-47-9, CAS 68515-73-1, or CAS 68439-46-3.

According to particularly preferred embodiments, the at least one amphiphile molecule comprises at least one natural surfactant found in individuals, more preferably at least one lung surfactant and/or pulmonary surfactant (e.g., dipalmitoylphosphatidylcholine (DPPC) CAS No. 2644-64-6)), even more preferably at least one natural surfactant found in aveoli. Pulmonary surfactant is a surface-active lipoprotein complex formed by type II alveolar cells. The proteins and lipids that make up the surfactant have both hydrophilic and hydrophobic regions. One advantage of using a natural surfactant is reducing risks of toxicity, bioactivity, or related risks. According to another embodiment, a synthetic version and/or modified version of the natural surfactant is used in the therapeutic composition.

According to other preferred embodiments, the at least one foaming agent comprises a natural foaming agent, for example the natural foaming agent derived from the Soap Bark tree.

Preferably, the therapeutic methods and/or compositions are administered is used to prevent or impede the onset, development, progression, and/or severity of an infection, illness and/or disease, or a symptom thereof.

Preferably, the at least one foaming agent is delivered in an aqueous medium (e.g., aerosolized or in liquid form), preferably buffered to within 1 pH of physiologic pH (7.2).

In some embodiments of the invention, the surfactant is a non-ionic surfactant or zwitterionic surfactant. In some embodiments, the surfactant has a hydrophile lipophile balance (HLB) from about 12 to about 15.

One of ordinary skill in the art would understand the therapeutic compositions and methods described herein can be adapted or configured by optimizing the amount administered and the manner of administration, along with optimizing the composition, in particular the foaming agents and other components used, in view of the area of anatomy of treatment and how that anatomy reacts to particles including treatment time in the target area of interest. Another aspect of the invention relates to a breathing system for treating an individual having at least one lower respiratory system region with one or more respiratory symptoms, the system comprising:
  (a) at least one gas source for providing air and/or oxygen to the individual; and
  (b) at least one source for administrating at least one foaming agent to the at least one lower respiratory system region.

Another aspect of the invention relates to a breathing system for treating an individual having at least one lower respiratory system region with one or more respiratory symptoms, the system comprising:
  (a) at least one gas source for providing air and/or oxygen to the individual; and
  (b) at least one source for applying energy to the at least one lower respiratory system region in an effective amount and for an effective time period to reduce the symptoms.

Another aspect of the invention relates to a breathing system for treating an individual having at least one lower respiratory system region with one or more respiratory symptoms, the method comprising:
  (a) at least one gas source for providing air and/or oxygen to the individual;
  (b) at least one source for administrating at least one foaming agent to the at least one lower respiratory system region; and
  (c) at least one source for applying energy to the at least one lower respiratory system region in an effective amount and for an effective time period to reduce the symptoms.

Preferably, the at least one gas source for providing air and/or oxygen to the individual comprises at least one catheter configured to be placed in an airway of the patient.

Preferably, the system comprises a tube configured to be placed in an airway of the patient and configured to administer the gas, aerosol and/or liquid comprising the at least one foaming agent.

Preferably, the system comprises a tube or other conduit configured to be placed in an airway of the patient and configured to administer the gas, aerosol and/or liquid comprising the at least one foaming agent.

Preferably, the system comprises at least one tube or other conduit configured to suction carbon dioxide and, optionally, also bubbles and/or foam and/or liquid and/or mucus from the lung airways.

Preferably, the system is configured to ventilate the patient by delivering gas at a positive pressure and flow rate sufficient to increase lung pressure during an inspiration phase of the patient and/or configured to deliver gas (preferably via a conduit or lumen) to assist in the removal of CO2-rich gas during an expiration phase.

Preferably, the system is configured to administer the foaming agent(s) at least once, in bursts, continually and/or for a period of time or periods of time. Specifically, according to preferred embodiments, after an effective amount of foaming agent has been delivered, the administration of foaming agent is paused, while the breathing system continues to provide air and/or oxygen to the individual while, optionally, the external energy is applied to the target region, and the steps are preferably repeated to improve the outcome for the patient.

Preferably, the at least one foaming agent is administered to a portion of a lung or one lung at a time.

In the description above, for purposes of explanation only, specific nomenclature is set forth to provide a thorough understanding of the present disclosure. However, it will be apparent to one skilled in the art that these specific details are not required to practice the teachings of the present disclosure. Moreover, the various features of the representative examples and the dependent claims may be combined in ways that are not specifically and explicitly enumerated in order to provide additional useful embodiments of the present teachings. It is also expressly noted that all value ranges or indications of groups of entities disclose every possible intermediate value or intermediate entity for the purpose of original disclosure, as well as for the purpose of restricting the claimed subject matter. It is also expressly noted that the method steps, parameters and the compositions described herein are designed to help to understand how the present teachings are practiced, but not intended to limit the invention.

The scope of the present compositions, systems and methods, etc., may include both means plus function and step plus function concepts. However, the claims are not to be interpreted as indicating a "means plus function" relationship unless the word "means" is specifically recited in a claim, and are to be interpreted as indicating a "means plus function" relationship where the word "means" is specifically recited in a claim. Similarly, the claims are not to be interpreted as indicating a "step plus function" relationship unless the word "step" is specifically recited in a claim, and are to be interpreted as indicating a "step plus function" relationship where the word "step" is specifically recited in a claim.

It is understood that the embodiments described herein are for the purpose of elucidation and should not be considered limiting the subject matter of the disclosure. Various modifications, uses, substitutions, combinations, improvements, methods of productions without departing from the scope or spirit of the present invention would be evident to a person skilled in the art.

The invention claimed is:

1. A method of treating an individual having at least one lower respiratory system region with at least one respiratory symptom, the method comprising:
  (a) administering at least one foaming agent to the at least one lower respiratory system region, wherein the at least one lower respiratory system region includes at least one alveolus having excess alveolar edema fluid; and
  (b) applying external energy to the at least one lower respiratory system region including to at least one alveolus in an effective amount and for an effective time period to generate bubbles and/or foam within the at least one lower respiratory system region to reduce the amount of excess alveolar edema fluid within the at least one alveolus.

2. The method of claim 1, wherein the at least one respiratory symptom is caused by a virus infection.

3. The method of claim 1, wherein the at least one foaming agent is delivered using a ventilator.

4. The method of claim 1, wherein the at least one foaming agent is delivered in an aerosol.

5. The method of claim 1, wherein the at least one foaming agent is delivered in a liquid and the method further comprises removing excess alveolar edema fluid, foam and/or bubbles from the at least one lower respiratory system region.

6. The method of claim 5, further comprising aerosolizing the liquid comprising the at least one foaming agent prior to said administering.

7. The method of claim 1, wherein the at least one foaming agent is effectively delivered as an aerosol in sufficient quantity and effective amount to exert a therapeutic response.

8. The method of claim 1, wherein the external energy comprises: (i) acoustic/sound waves; (ii) vibrational energy; (iii) magnetic waves; (iv) electromagnetic waves; (v) breathing system parameter variations; (vi) temperature variations; and/or (v) chemical energy.

9. The method of claim 1, wherein the external energy is at least one sound wave and/or vibrational energy.

10. The method of claim 1, wherein the applying of external energy generates at least one bubble from the excess alveolar edema fluid within at least one alveolus.

11. The method of claim 1, wherein the at least one foaming agent comprises one or more lung surfactants and/or one or more pulmonary surfactants.

12. A method of treating an individual having at least one lower respiratory system region with acute respiratory distress syndrome (ARDS) symptoms including at least one alveolus having excess alveolar edema fluid, the method comprising administering at least one foaming agent and applying external energy to the at least one lower respiratory system region in an effective amount and for an effective time period to generate bubbles and/or foam within the at least one lower respiratory system region to reduce at least one of said acute respiratory distress syndrome (ARDS) symptoms.

13. The method of claim 12, wherein the at least one lower respiratory system region includes at least one alveolus having excess alveolar edema fluid in amounts sufficient to inhibit gas exchange.

14. The method of claim 12, wherein the at least one acute respiratory distress syndrome (ARDS) symptoms is caused by a virus infection.

15. The method of claim 12, wherein the external energy is administered using a vibration vest.

16. The method of claim 15, wherein the applying the external energy to the at least one lower respiratory system region is in an effective amount and for an effective time period to reduce excess alveolar edema fluid.

17. The method of claim 12, wherein the reduce the at least one acute respiratory distress syndrome (ARDS) symptoms comprises reducing the excess alveolar edema fluid.

18. The method of claim 12, wherein the applying the external energy to the at least one lower respiratory system region is in an effective amount and for an effective time period to allow for increased oxygen/carbon dioxide exchange.

19. The method of claim 12, wherein said applying of said external energy to the at least one lower respiratory system region comprises applying a first source of the external energy and applying a second source of the external energy.

20. A method of treating an individual having at least one lower respiratory system region with acute respiratory distress syndrome (ARDS) symptoms, the method comprising:

(a) administering one or more lung surfactants and/or one or more pulmonary surfactants to the at least one lower respiratory system region, wherein the at least one lower respiratory system region includes at least one alveolus having excess alveolar edema fluid;

(b) applying sound wave and/or vibrational energy to the at least one lower respiratory system region including to the at least one alveolus in an effective amount and for an effective time period to reduce the amount of excess alveolar edema fluid within the at least one alveolus; and (c) removing excess alveolar edema fluid from the at least one lower respiratory system region, wherein the method results in increased oxygen/carbon dioxide exchange within the at least one lower respiratory system region.

* * * * *